US011213283B2

(12) United States Patent
Shah

(10) Patent No.: US 11,213,283 B2
(45) Date of Patent: Jan. 4, 2022

(54) IMPLANTABLE PROSTHETIC DEVICE

(71) Applicant: C.R. Bard, Inc., Murray Hill, NJ (US)

(72) Inventor: Devang Vijay Shah, Franklin, MA (US)

(73) Assignee: C.R. Bard, Inc., Murray Hill, NJ (US)

( * ) Notice: Subject to any disclaimer, the term of this patent is extended or adjusted under 35 U.S.C. 154(b) by 365 days.

(21) Appl. No.: 15/935,793

(22) Filed: Mar. 26, 2018

(65) Prior Publication Data
US 2018/0280007 A1 Oct. 4, 2018

Related U.S. Application Data

(60) Provisional application No. 62/477,744, filed on Mar. 28, 2017.

(51) Int. Cl.
*A61B 17/00* (2006.01)
*A61B 17/34* (2006.01)

(52) U.S. Cl.
CPC .......... *A61B 17/0057* (2013.01); *A61B 17/34* (2013.01); *A61B 17/3417* (2013.01); *A61B 17/3421* (2013.01); *A61B 2017/0065* (2013.01); *A61B 2017/00579* (2013.01); *A61B 2017/00637* (2013.01); *A61B 2017/00646* (2013.01);
(Continued)

(58) Field of Classification Search
CPC . A61B 17/0057; A61B 17/34; A61B 17/3417; A61B 17/3421; A61B 2017/00579; A61B 2017/00637; A61B 2017/00646; A61B 2017/0065; A61B 2017/00654; A61B 2017/00884;
(Continued)

(56) References Cited

U.S. PATENT DOCUMENTS 4,838,280 A    6/1989  Haaga
5,320,639 A *  6/1994  Rudnick ............ A61B 17/0057
                                                        604/15
(Continued)

FOREIGN PATENT DOCUMENTS

WO    WO 2016/077444 A1    5/2016
WO    WO 2016/083606 A1    6/2016

OTHER PUBLICATIONS

International Search Report and Written Opinion for International Application No. PCT/US2018/024324, dated Jun. 25, 2018.
(Continued)

*Primary Examiner* — Erich G Herbermann
(74) *Attorney, Agent, or Firm* — Wolf, Greenfield & Sacks, P.C.

(57) ABSTRACT

A prosthesis and a method of plugging or covering a trocar tract with the prosthesis is disclosed. The prosthesis includes a tubular body having a proximal end and a distal end, a respective opening at each end, and a channel extending between the proximal end of the tubular body and the distal end of the tubular body. The prosthesis is removably mounted along a trocar. The trocar is removable from the prosthesis such that the prosthesis is left at the trocar tract when the trocar is removed from the tract. The prosthesis includes a delivery configuration and a deployed configuration. In the deployed configuration, the opening at the distal end of the tubular body is smaller than the opening at the proximal end of the tubular body.

40 Claims, 14 Drawing Sheets

(52) U.S. Cl.
CPC ............... *A61B 2017/00654* (2013.01); *A61B 2017/00884* (2013.01); *A61B 2017/00893* (2013.01); *A61B 2017/3484* (2013.01)

(58) Field of Classification Search
CPC .. A61B 2017/00893; A61B 2017/3484; A61B 17/3423; A61B 17/3462
See application file for complete search history.

(56) References Cited

U.S. PATENT DOCUMENTS

| | | | |
|---|---|---|---|
| 5,324,306 A | | 6/1994 | Makower et al. |
| 5,752,970 A | * | 5/1998 | Yoon ................. A61B 17/3421 604/167.03 |
| 6,228,063 B1 | | 5/2001 | Aboul-Hosn |
| 2004/0143281 A1 | * | 7/2004 | Hart ....................... A61B 17/34 606/185 |
| 2004/0170597 A1 | | 9/2004 | Beckman et al. |
| 2006/0100664 A1 | * | 5/2006 | Pai .................. A61B 17/00491 606/214 |
| 2007/0106319 A1 | | 5/2007 | Au et al. |
| 2008/0051675 A1 | | 2/2008 | Doorschodt |
| 2008/0058728 A1 | | 3/2008 | Soltz et al. |
| 2011/0224719 A1 | * | 9/2011 | Fortson .............. A61B 17/0057 606/213 |
| 2012/0016411 A1 | * | 1/2012 | Tuval ................. A61B 17/0057 606/213 |
| 2012/0022585 A1 | * | 1/2012 | Atanasoska ........ A61B 17/0057 606/213 |
| 2012/0190933 A1 | * | 7/2012 | Kleyman ............ A61B 17/3423 600/207 |
| 2012/0209078 A1 | * | 8/2012 | Pribanic ............. A61B 17/3423 600/208 |
| 2013/0245677 A1 | | 9/2013 | Sargeant et al. |
| 2014/0163609 A1 | | 6/2014 | Solem |
| 2014/0276437 A1 | | 9/2014 | Hart et al. |

OTHER PUBLICATIONS

International Preliminary Report on Patentability for International Application No. PCT/US2018/024324, dated Oct. 10, 2019.

\* cited by examiner

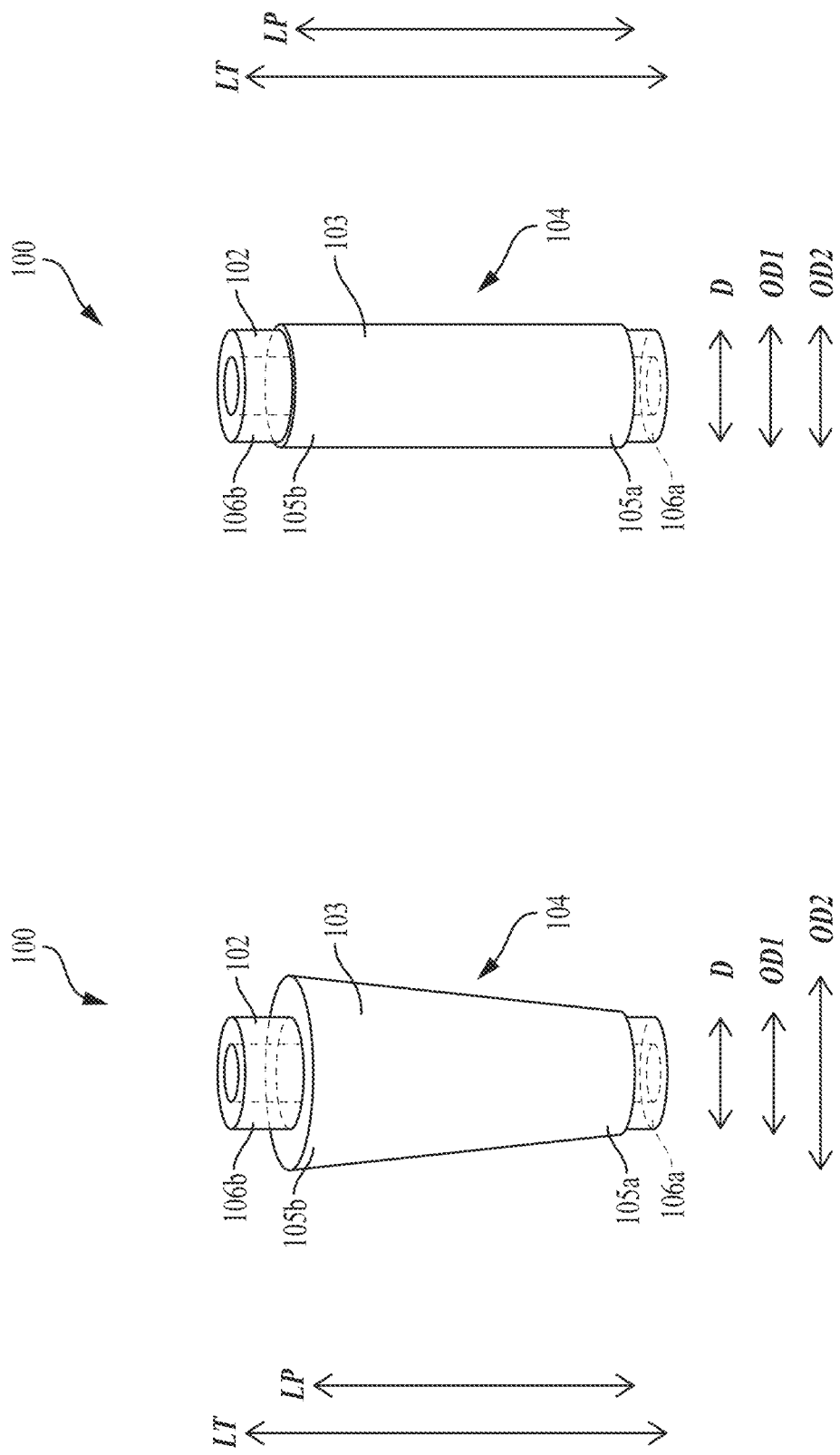

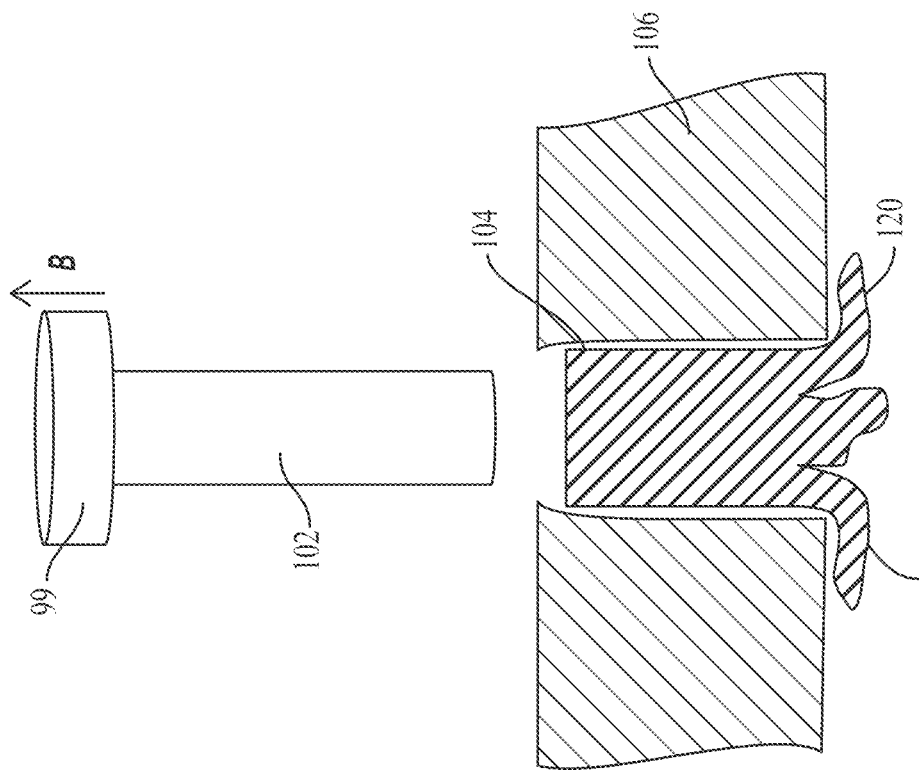
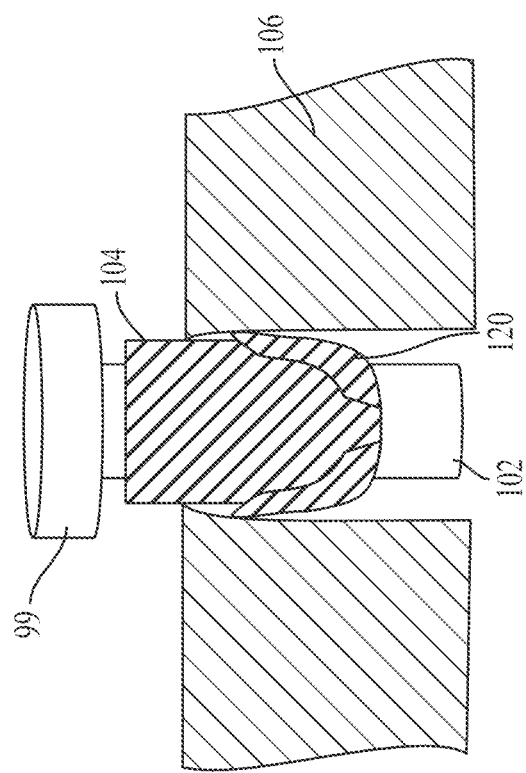

IMPLANTABLE PROSTHETIC DEVICE

CROSS-REFERENCE TO RELATED APPLICATIONS

This application claims priority under 35 U.S.C. § 119(e) to U.S. Provisional Application No. 62/477,744, entitled "IMPLANTABLE PROSTHETIC DEVICE" and filed Mar. 28, 2017, the contents of which are incorporated herein by reference in its entirety.

FIELD

The present invention relates to an implantable prosthesis and, more particularly, to a prosthesis for repairing a cannula or trocar tract after completion of a medical procedure along the tract.

BACKGROUND

During minimally invasive surgeries, such as laparoscopies, a surgeon makes one or more incisions and inserts a trocar into a body cavity via one of the incisions. Specialized instruments may then be inserted through the trocar and into the body cavity to conduct specific procedures. At the conclusion of the MIS, the trocar tract is closed to prevent complications, such as hernias, infections, and fluid loss. Typically, such tracts are closed by suturing or stapling the incision. Biomedical adhesives also have been used to prevent fluid leakage from the tract.

SUMMARY

According to one embodiment, an implantable prosthesis in combination with a trocar is disclosed. The combination includes a trocar with a proximal end and a distal end, a respective opening at each end, and a channel extending between the proximal opening and the distal opening for passing one or more surgical instruments through the trocar. The combination also includes a prosthesis removably mountable along an outer surface of the trocar, the prosthesis including a tubular body having a proximal end and a distal end, a respective opening at each of the proximal end and the distal end of the tubular body, and a channel extending between the proximal end and the distal end of the tubular body, wherein the prosthesis includes a delivery configuration where the prosthesis is removably mounted along the outer surface of the trocar and a deployed configuration where the prosthesis is removed from the trocar, wherein, in the deployed configuration, the opening at the distal end of the tubular body is smaller than an opening at the proximal end of the tubular body.

According to another embodiment, a prosthesis for plugging or covering a trocar tract is disclosed. The prosthesis includes a tubular body having a proximal end and a distal end, a respective opening at each of the proximal end and the distal end of the tubular body, and a channel extending between the proximal end and the distal end of the tubular body. The prosthesis includes a delivery configuration where the prosthesis is removably mounted along the outer surface of a trocar and a deployed configuration where the prosthesis is removed from the trocar. In the deployed configuration, the opening at the distal end of the tubular body is smaller than an opening at the proximal end of the tubular body.

According to another embodiment, a method includes providing a trocar with a proximal end and a distal end, a respective opening at each end, and a channel extending between the proximal opening and the distal opening for passing one or more surgical instruments through the trocar. The method also includes removably mounting a prosthesis along an outer surface of the trocar, the prosthesis having a tubular body with a distal end and a proximal end, a respective opening at each of the proximal end and the distal end of the tubular body, and a channel extending between the proximal end and the distal end of the tubular body, wherein the prosthesis includes a delivery configuration where the prosthesis is removably mounted along the outer surface of the trocar and a deployed configuration where the prosthesis is removed from the trocar, wherein, in the deployed configuration, the opening at the distal end of the tubular body is smaller than the opening at the proximal end of the tubular body.

It should be appreciated that the foregoing concepts, and additional concepts discussed below, may be arranged in any suitable combination, as the present disclosure is not limited in this respect.

The foregoing and other aspects, embodiments, and features of the present teachings can be more fully understood from the following description in conjunction with the accompanying drawings.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 2A is a perspective view of a prosthesis removably mounted along a trocar according to one embodiment;

FIG. 2B is a perspective view of a prosthesis removably mounted along a trocar according to another embodiment;

FIGS. 10A and 10B illustrated delivery and deployment configurations of a prosthesis according to one embodiment;

DETAILED DESCRIPTION

Figures 1A, 1B:
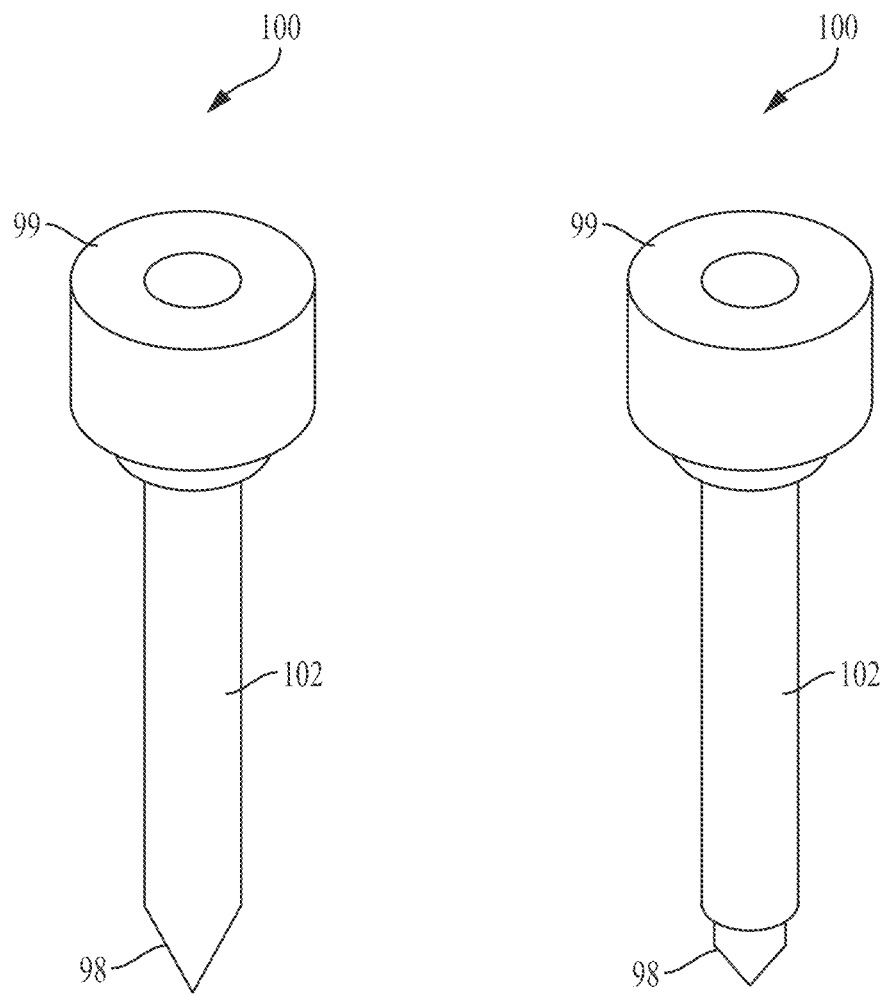
FIG. 1A is a perspective view of a trocar according to one embodiment.
FIG. 1B is a perspective view of a trocar according to one embodiment.

Minimally invasive surgeries ("MIS") are less invasive alternatives to open surgical procedures that are used to treat similar conditions. For example, an MIS may lead to lower patient morbidity, less pain, and faster recover times.

During a typical MIS, a surgeon makes one or more incisions and inserts a trocar into a body cavity via one of the incisions. Such a trocar may include a seal, a cannula and an obturator. Specialized instruments may then be inserted through the trocar and into the body cavity to conduct specific procedures. At the conclusion of the MIS, the trocar tract is closed to prevent complications, such as hernias, infections, and fluid loss. Traditional closure techniques include suturing or stapling of the incision. Biomedical adhesives also have been used to prevent fluid leakage from the tract.

Applicant has realized that by providing a prosthesis that is removably mounted along a trocar, the prosthesis being removable from the trocar when the trocar is removed from a body cavity, various advantages may be realized. For example, the prosthesis may be left in a trocar tract to plug and/or cover the tract when the trocar is removed from the tract. In some embodiments, such a prosthesis may be deployed without requiring additional time, steps, materials (e.g., sutures) and/or instruments when the trocar is removed from the tract. As will be appreciated, removal of the trocar will leave the prosthesis in place for repairing the tract. However, in other embodiments, additional materials, such as sutures, or instruments may be used to secure the prosthesis at the tract after removal of the trocar.

To that end, embodiments disclosed herein include an implantable prosthesis with a tubular body removably mounted along an outer surface of a trocar, the body having a distal end and a proximal end, with a respective opening at each end and a channel extending between the proximal end and the distal end of the tubular body. For example, the channel may extend between the opening at the distal end of the tubular body and the opening at the proximal end of the tubular body. In some embodiments, the body is arranged to remain mounted along the trocar while the trocar is inserted and positioned in the trocar tract (e.g., for delivery of the prosthesis) and to be removable from the trocar when the trocar is removed from the tract (e.g., for deployment of the prosthesis). In such embodiments, the prosthesis includes a delivery configuration where the prosthesis is removably mounted along the trocar and a deployed configuration where the prosthesis is removed from the trocar. In the deployed configuration, the opening at the distal end of the prosthesis body may be smaller than the opening at the proximal end of the body. In the deployed configuration, the opening at the distal end of the prosthesis body may be closed, which may seal the trocar tract. In some embodiment, this may create a fluid-tight seal at the trocar tract.

For purposes herein, the trocar means a trocar (e.g., an integrally formed instrument) that is placed along a tract through tissue, such as may be formed by a trocar, incision, or otherwise, or naturally formed. The trocar also means a trocar and cannula assembly, such as one where the trocar may be removed to leave the trocar cannula in the trocar tract, or a cannula. In such embodiments, the prosthesis may be removably mounted along the trocar such that when the trocar is removed from the tract, the prosthesis remains in the tract.

In some embodiments, the prosthesis body is arranged to automatically assume the deployed configuration. For example, the distal end of the body may be formed of an elastic material that contracts when the trocar is removed from the prosthesis. As another example, the distal end may include one or flaps arranged to overlap one another when the trocar is removed from the prosthesis. As will be appreciated, closing of the distal end of the prosthesis also may occur manually. For example, a medical professional, such as a surgeon, may tighten a suture extending around a periphery of the distal end of the body to close the opening at the distal end.

In some embodiments, the prosthesis includes one or more attachment members for attaching the body of the prosthesis to the tissue surrounding the trocar tract when the trocar is inserted and positioned in the tract. In some embodiments, the attachment members include one or more barbs and/or one or more flaps. The prosthesis also may include an adhesive arranged to attach the prosthesis body to the tissue at the tract. As will be appreciated, the attachment members and/or adhesive may attach the prosthesis body to the tissue such that the trocar is automatically removable from the prosthesis when the trocar is removed from the tract. As will be further appreciated, once the trocar is removed from the prosthesis, the prosthesis may take on the deployed configuration to seal the tract and/or to allow for tissue ingrowth.

Turning now to the figures, FIGS. 1A and 1B show a trocar 100 according to embodiments of the present disclosure. As shown in these views, the trocar 100 includes a cannula 102 used to access a body cavity of a patient during an MIS (see, e.g., FIGS. 4-7), a seal 99, and an obturator 98. The obturator 98, or puncturing device, may be used to penetrate the body, such as by piercing an abdominal wall, to allow the trocar to be placed in a trocar tract. In such embodiments, one or more surgical instruments, such as laparoscopic instruments, may be passed through the trocar and into a body cavity.

As will be appreciated, and as shown in FIG. 1A, the trocar may be an integrally formed instrument. For example, the seal, obturator and cannula may be integrally formed, with the obturator 98 located at a distal end of the cannula 102 and the seal 99 located at the proximal end of the cannula 102. In other embodiments, as shown in FIG. 1B, the trocar may include an assembly with a cannula that is removable. In such embodiments, the obturator 98 may include a tubular body, with a puncturing device at a distal end, the obturator being inserted into and extending beyond a distal end of the cannula for puncturing. As will be appreciated, the obturator may be removed from the cannula after puncturing, leaving the cannula in the trocar tract. In some embodiments, the seal 99 may be integrally formed with the cannula 102.

Figure 1C:
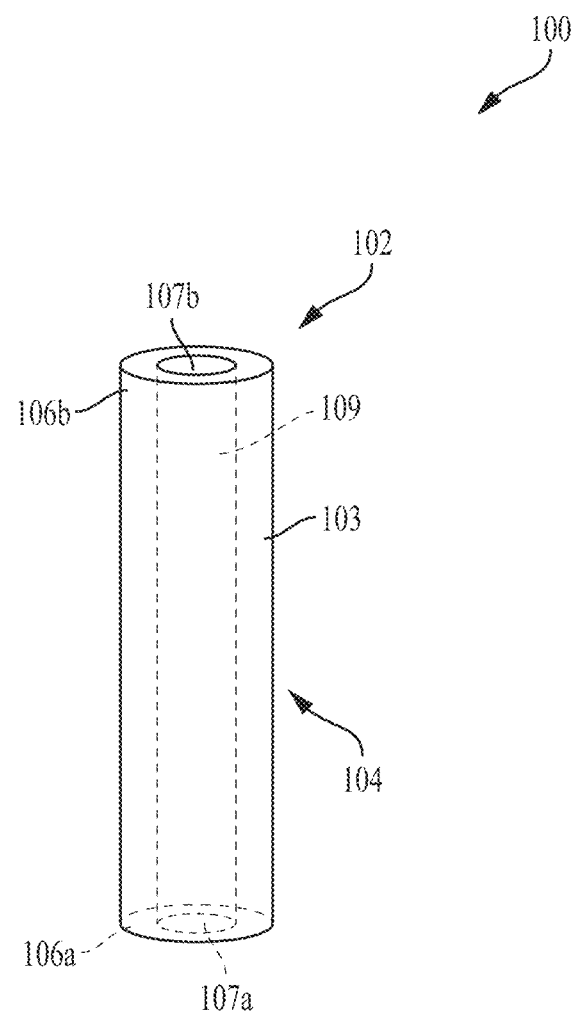
FIG. 1C is a perspective view of a trocar according to one embodiment.

Turning now to FIG. 1C, which shows a trocar according to some embodiments. As shown in this view, the trocar includes a cannula 102 having a tubular body or shaft with a distal end 106a and a proximal end 106b. In some embodiments, the tubular body may have a uniform cross-section between the distal and proximal ends, such as the circular cross-section shown in FIG. 1C. In some embodiments, the cannula may be thin-walled.

As also shown in FIG. 1C, the proximal and distal ends 106b, 106a of the cannula have respective openings 107b, 107a, with a channel 109 extending between the distal opening and the proximal opening for passing one or more surgical instruments through the trocar. In some embodiments, the shape and size of the distal and proximal openings 107a, 107b are the same. In such an embodiment, the channel 109 may have a uniform cross-section between the distal and proximal ends, such as the shown circular cross-section. The openings also may have different shapes and sizes, with the cross-section of the channel varying between the proximal and distal ends. As will be appreciated, the channel may have other suitable shapes and configurations in other embodiments.

According to one aspect of the disclosure, and as shown in FIGS. 2A and 2B, in some embodiments, a prosthesis may be removably mounted along the trocar. For example, as shown in these views, the prosthesis 104 may include a prosthesis body 103 that is removably mounted along an outer surface of the trocar cannula 102.

For purposes herein, being removably mounted along the trocar means that the prosthesis is arranged to remain mounted along the trocar when the trocar is inserted and positioned in the trocar tract, but is otherwise removable, such as when the trocar is removed from the body. In some embodiments, the prosthesis is mounted along the trocar such that the prosthesis does not roll up or otherwise get pushed up against the trocar seal during insertion. In some embodiments, the prosthesis is mounted along the trocar such that the prosthesis does not move substantially relative to the trocar during insertion. For example, the prosthesis may not move substantially out of the delivery configuration. As will be appreciated, in embodiments in which the prosthesis does move substantially relative to the trocar, the prosthesis may be manually moved back into the delivery configuration, such as by a surgeon with a surgical instrument. As will be further appreciated, in some embodiments, the body may move slightly upon insertion of the trocar into the body. For example, the prosthesis body may move less than about 5% of a length of the trocar during insertion of the trocar.

In some embodiments, being removable from the trocar means that the prosthesis is automatically left in the tract when the trocar is removed from the prosthesis. For example, the prosthesis may become attached to the tract after the trocar is inserted and positioned in the tract such that the force of attachment is greater than the force applied to pull the trocar from the tract. The prosthesis also may be manually removable from the trocar before or during removal of the trocar from the body. For example, a surgeon may use a second surgical instrument to pull the prosthesis off of the trocar when the trocar is being removed from the tract.

In some embodiments, the entire prosthesis body is removably attached to the trocar. For example, as shown in FIG. 2B, the prosthesis may include an elastic sleeve that fits snugly around the trocar. In other embodiments, at least a portion of the body may be attached to the trocar. For example, in FIG. 2A, only the distal portion, such as the distal end of the prosthesis body, may be attached to the trocar, with the proximal end not attached to the trocar. In such an example, the prosthesis is still mounted along the trocar even though only the distal end is attached to the trocar cannula.

As will be appreciated, the prosthesis 104 may be removably attached to the trocar via any suitable manner. In some embodiments, the prosthesis body 103 is arranged to fit snugly around the exterior surface of the trocar. For example, the body 103 may be formed of an elastic material, with the body 103 being stretched to fit around the exterior surface of the trocar. In another embodiment, one or more engagement features on the body 103 may engage with one or more corresponding engagement features on the trocar for removably attaching the prosthesis 104 to the trocar. Such engagement features may be placed on any suitable part of the prosthesis body and/or trocar. For example, the trocar may include a groove arranged to receive an elastic loop or one or more flexible tabs on the prosthesis. As another example, the trocar may have one or more clips for clipping the prosthesis to the trocar. The trocar also may have other snaps or fasteners that engage with corresponding snaps or fasteners on the prosthesis for attaching the prosthesis to the trocar.

In other embodiments, the prosthesis body 103 may be attached to the trocar with an adhesive. The adhesive may be applied at one portion or at multiple portions of the prosthesis body and/or trocar. In some embodiments, the adhesive may be biocompatible and dissolve after a desired time interval so that the trocar may be thereafter removed from the prosthesis.

As shown in FIGS. 2A-2D, the prosthesis 104 may include a tubular body 103 with a distal end 105a and a proximal end 105b, and a respective opening 111a, 111b at each end. A channel 113 may extend between the distal end of the tubular body and the proximal end of the tubular body, such as between the opening 111a at the distal end and the opening 111b at the proximal end.

Figure 2D:
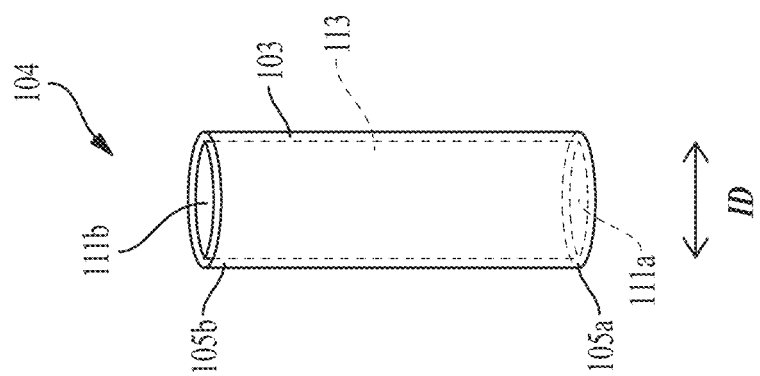
FIG. 2D is a perspective view of the prosthesis of FIG. 2B.
Figure 2C:
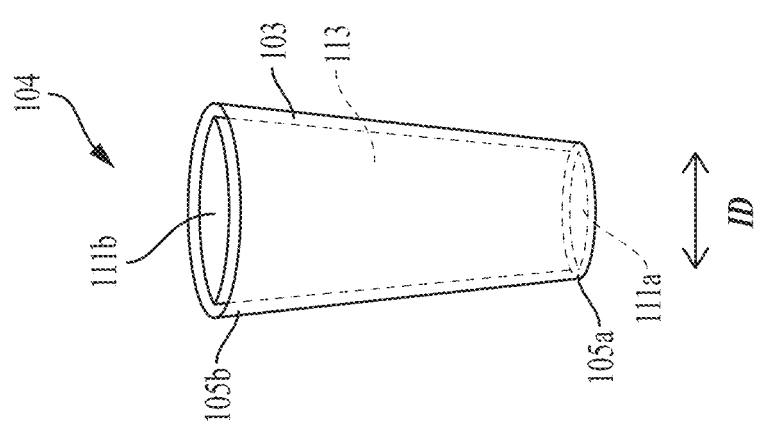
FIG. 2C is a perspective view of the prosthesis of FIG. 2A.

In some embodiments, the channel may be straight or it may be curved. As shown in FIGS. 2A and 2C, the size of the channel may vary between the distal end and the proximal end. The size of the channel also may be constant between the distal and proximal ends, as shown in FIGS. 2B and 2D. The shape of the channel also may vary between the distal and proximal ends, or the shape may be constant.

As will be appreciated, the channel is sized to receive the trocar (e.g., the cannula). For example, the inner dimension ID of the channel (e.g., the inner diameter in embodiments having a channel with a circular cross section) may be greater than the diameter D of the trocar. In such an example, the inner dimension of the channel may only be slightly larger than a diameter D of the trocar (see FIGS. 2A and 2B) such that at least a portion of the prosthesis fits snugly around the trocar. As will be further appreciated, the size and shape of the channel may change when the trocar is inserted into and removed from the prosthesis. For example, in the delivery configuration, the inner dimension of the channel may be greater than the diameter of the trocar, while in the deployed configuration, the inner dimension of the channel may be smaller than the diameter of the trocar.

As shown in FIG. 2A, in some embodiments, the distal end 105a of the prosthesis body 103 has an outer dimension OD1 that is smaller than the outer dimension OD2 of the proximal end 105b. For purposes herein, the outer dimension of the prosthesis body includes a distance between an outer-most portion of a first side of the body and an outer-most portion of a second, opposite, side of the body. For example, in embodiments in which the prosthesis body has a circular cross-section, the outer dimension includes an outer diameter of the prosthesis body. In other embodiments, as shown in FIG. 2B, the outer dimensions OD1, OD2 of the distal and proximal ends 105a, 105b of the body also may be the same.

As with the channel, the prosthesis may be straight or it may be curved. The shape and size of the prosthesis may be constant between the proximal and distal ends, although the shape and size may vary between ends. The shape and size of the prosthesis also may change as the trocar is inserted into and removed from the prosthesis. For example, in the delivery configuration, the outer dimension of at least a portion of the prosthesis may be greater than the diameter of the trocar, while in the deployed configuration, the outer dimension of at least a portion of the prosthesis may be smaller than the diameter of the trocar.

In some embodiments, as shown in these views, the end of the prosthesis body 103 may be substantially perpendicular to the length (and longitudinal axis) of the prosthesis. The end of the prosthesis body also may have other suitable shapes. For example, the end of each prosthesis body may be slanted or curved with respect to the length of the prosthesis. In another configuration, the prosthesis may have an A-line shape, with one end larger than the other.

As will be appreciated, although the shape of the channels in FIGS. 2C and 2D correspond to the shape of the prosthesis bodies (e.g., a frustoconical shaped channel and body in FIG. 2C and a cylindrical shaped channel and body in FIG. 2D), the shapes of the channel need not correspond to the shape of the body. For example a prosthesis body may be cylindrical, such as in FIG. 2D, with a frustoconical shaped channel. As will be appreciated, in such embodiments, the wall thickness of the body may be uniform along the length of the prosthesis or may vary between the proximal and distal ends.

In some embodiments, the prosthesis may be mounted along (e.g., cover) an entire length of the trocar. In other embodiments, the body 103 need not cover the entire length of the trocar. For example, as shown in FIGS. 2A and 2B, a length of the prosthesis LP may be shorter than a length of the trocar LT. In such embodiments, the prosthesis may be positioned closer to the distal end than to the proximal end of the trocar, although the prosthesis also may be positioned equidistant between the proximal and distal ends. In any such arrangements, and as shown by way of example in FIGS. 2A and 2B, the proximal end 105b of the body 103 is still positioned closer to the proximal end 106b of the trocar (e.g., the trocar cannula 102) than the distal end of the trocar, and the distal end 105a of the body 103 is positioned closer to the distal end 106a of the trocar than to the proximal end 106b of the trocar.

Figure 3A:
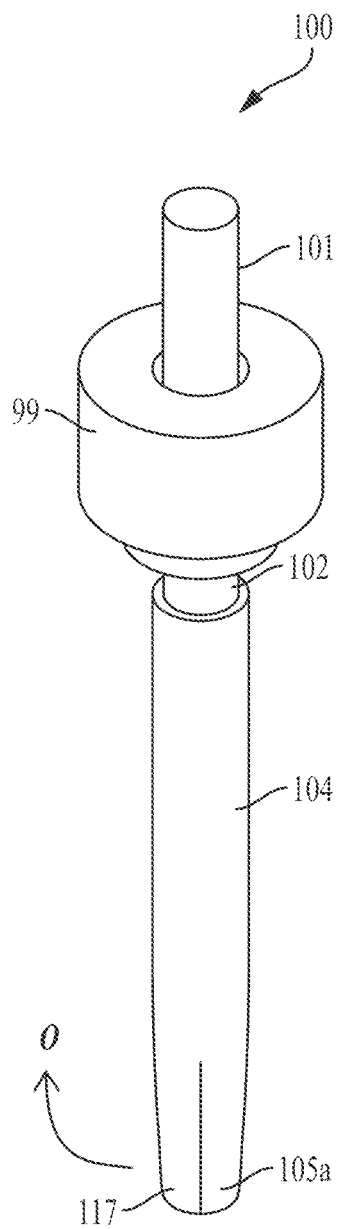
FIG. 3A is a perspective view of a prosthesis removably mounted along a trocar according to another embodiment.
Figure 3B:
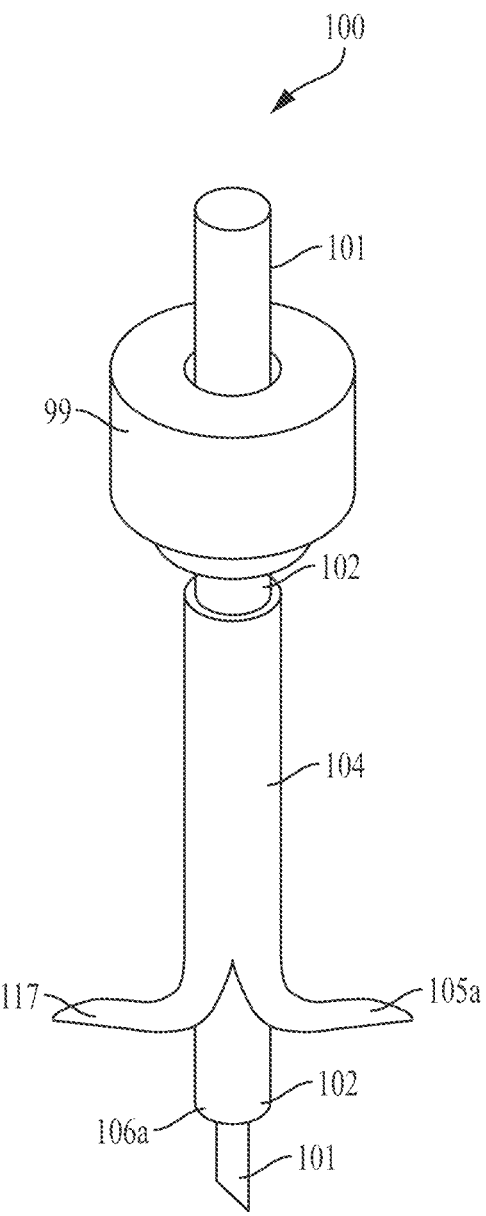
FIG. 3B is a perspective view of the assembly of FIG. 3A, with a surgical instrument being passed through the trocar.

In some embodiments, as also shown in FIGS. 2A and 2B, the prosthesis does not cover the distal end of trocar. In other embodiments, as shown in FIGS. 3A-3B, the prosthesis may be arranged to cover the distal end 106a of the trocar, such as the distal end of the cannula 102 (including an obturator). As shown in this view, in such embodiments, the distal end 105a of the prosthesis extends beyond the distal end 106a of the cannula 102. As will be appreciated, the distal end 105b of the prosthesis body 103 may be arranged to open and close, as needed during the MIS. For example, the distal end 105a of the prosthesis body 103 may include one or more flaps 117 that are moved outwardly (see the arrow labeled O in FIG. 3A) to open the distal end 105a of the body 103 when a surgical instrument 101 is passed through the trocar and into the body cavity (not shown). In such an example, when the surgical instrument 101 is removed, the flaps 117 may move in a direction opposite to the arrow O to close the distal end 105a of the body.

Turning now to FIGS. 4-7, which illustrate the trocar being inserted and positioned in a trocar track, and the prosthesis being removably mounted along the trocar. In such embodiments, the prosthesis may be used to plug or cover the tract when the trocar is removed from the prosthesis. As will be described in more detail below, the prosthesis may have a delivery configuration and a deployment configuration. For purposes herein, the delivery configuration corresponds to the arrangement of the prosthesis during insertion and positioning of the trocar in the trocar tract, when the prosthesis is removably mounted along the outer surface of the trocar. The deployed configuration corresponds to the arrangement of the prosthesis when the trocar is removed from the prosthesis, when the prosthesis is left at the tract to cover or plug the tract.

Figure 4:
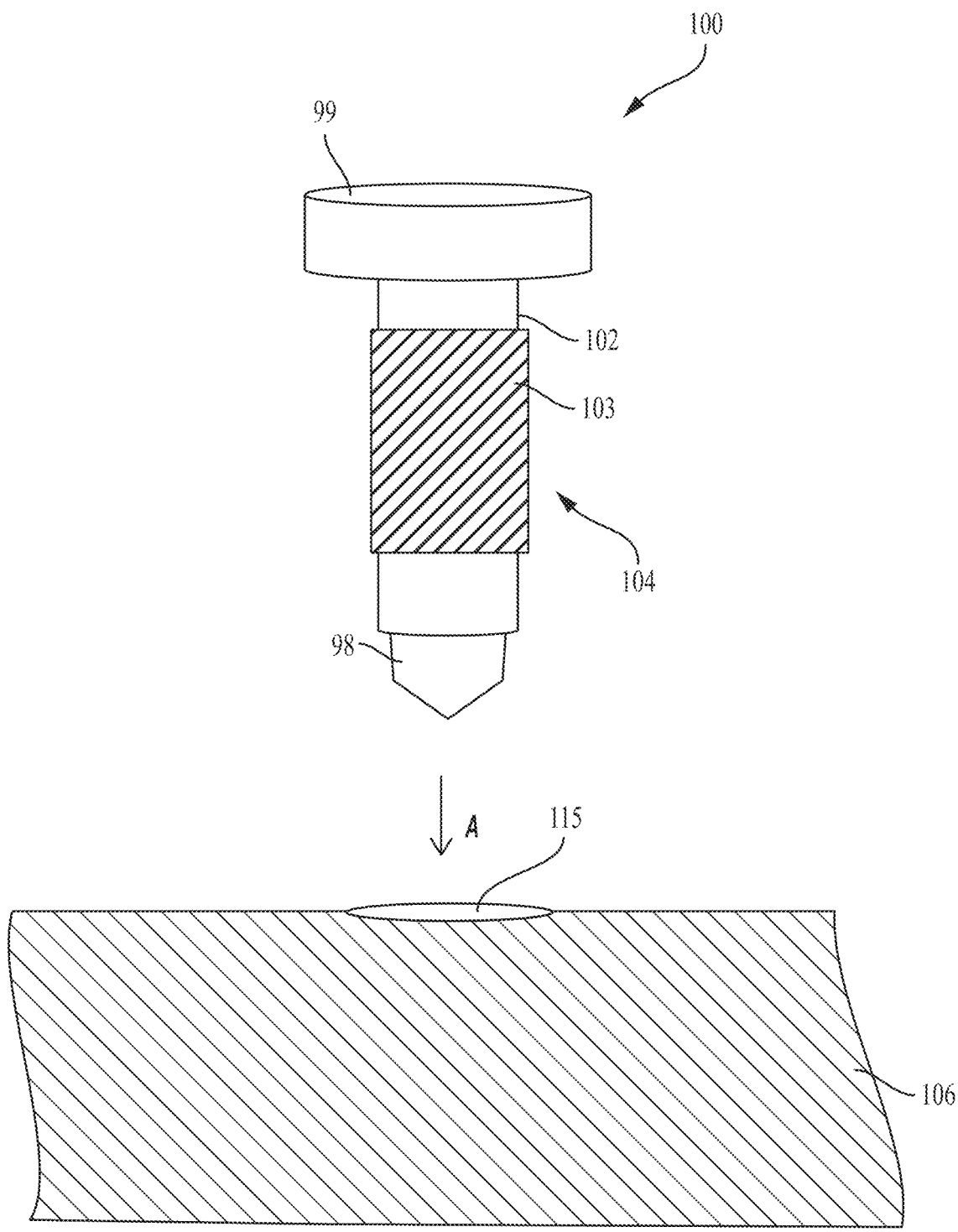
FIGS. 4-7 illustrate delivery and deployment configurations of a prosthesis according to one embodiment.

As shown in FIG. 4, in the delivery configuration, the prosthesis 104 is mounted along the trocar and readied for insertion into the body via an incision 115 in the tissue 106. As shown in this view, the prosthesis body 103 is removably mounted along the exterior surface of the trocar cannula 102 such that the body 103 will be positioned adjacent to the tissue 106 surrounding the trocar tract 108 (see FIG. 5) after insertion. During insertion, the cannula 102 is moved in a direction towards the incision 115 (see arrow A).

Figure 5:
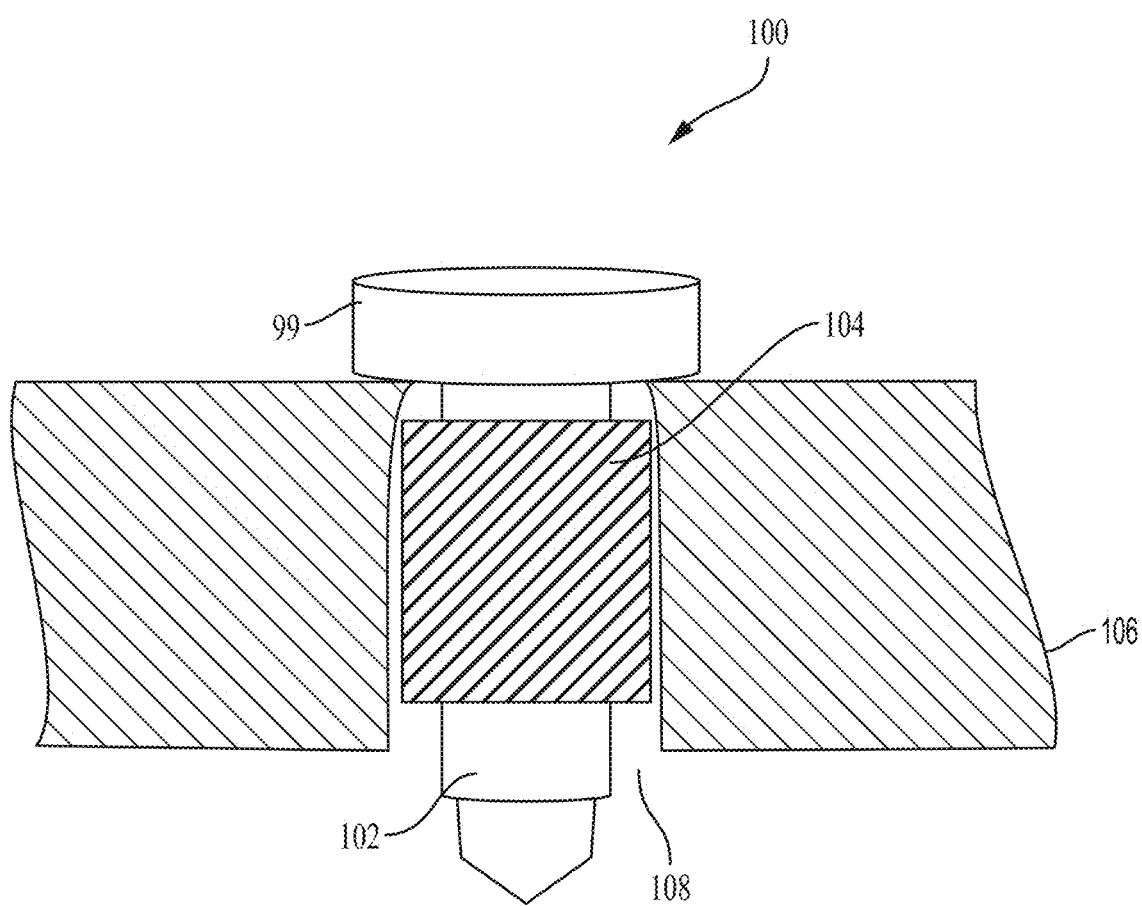

FIG. 5 illustrates the prosthesis in a delivery configuration, with the trocar inserted and positioned in a trocar tract 108. As shown in this view, once the trocar is positioned, the exterior surface of the prosthesis body 103 is located adjacent to the tissue 106 surrounding the tract 108. In such embodiments, the seal 99 is positioned adjacent to or against an outer surface of the tissue (e.g., an outer surface of the abdominal wall), with the trocar cannula 102 directed toward a body cavity for inserting surgical instruments.

In some embodiments, as shown in FIG. 5, the distal end 106a of the trocar may extend beyond the distal end of the trocar tract 108. The distal end of the trocar also may be flush with the distal end of the trocar tract. In such embodiments, depending on the placement of the trocar and the position of the prosthesis body on the trocar, the prosthesis body may or may not extend beyond the distal end of the trocar tract 108. The prosthesis body also may be flush with the distal end of the trocar tract.

Figure 6:
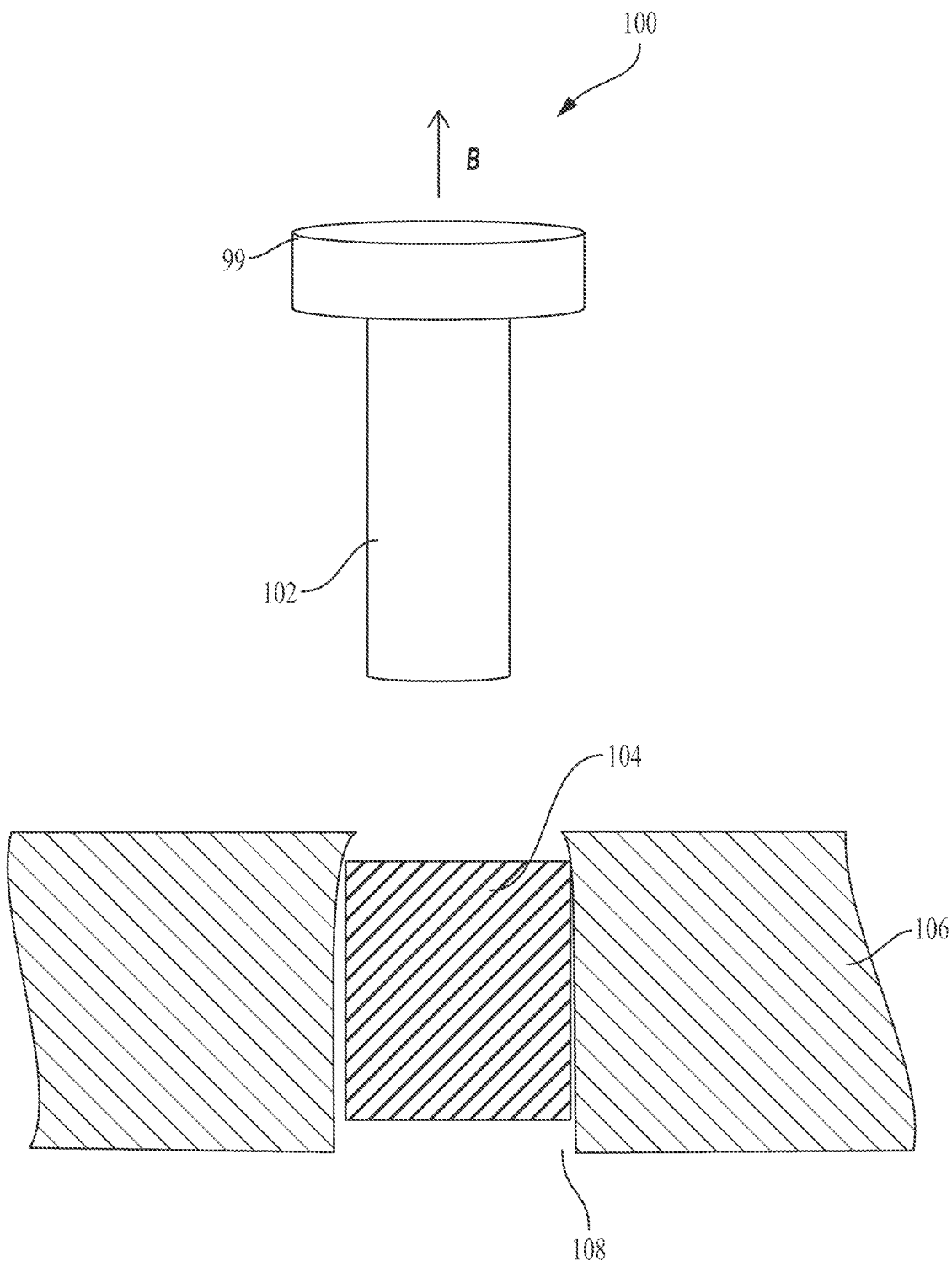
Figure 7:
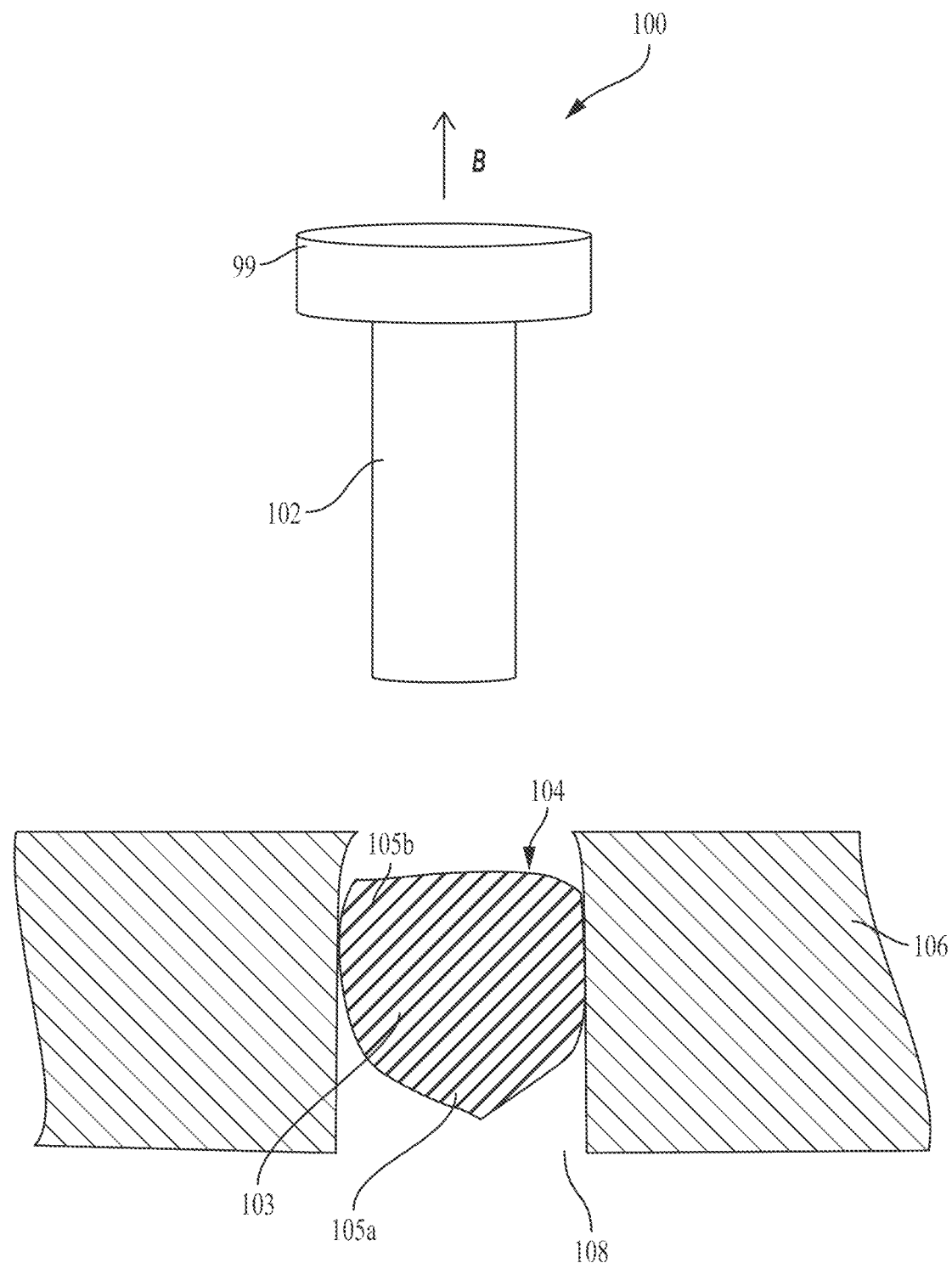

FIGS. 6 and 7 illustrate the prosthesis 104 in a deployed configuration, following the removal of the trocar (see arrow B). As shown in this view, when the trocar is removed from the trocar tract, the trocar is removed from the prosthesis 104, leaving the prosthesis in the trocar tract 108. In some embodiments, the prosthesis may be automatically removable from the trocar, or the prosthesis may be manually removed from the trocar. For example, as will be described in more detail below, the body may include one or more attachment members or an adhesive for attaching the prosthesis to the tissue. As will be appreciated, in such embodiments, the force holding the prosthesis to the tissue (e.g., via the attachment members or adhesive) is greater than the force pulling the trocar out of the body, causing the trocar to be removable from the prosthesis when the trocar is removed from the trocar tract. In other embodiments, the prosthesis may be manually removed from the trocar, such as via a surgeon and another surgical instrument.

FIG. 7 shows the prosthesis 104 in a deployed configuration, with the prosthesis body 103 sealing the trocar tract. For example, the distal end 105a of the prosthesis body 103 may be cinched such that the respective opening at the distal end of the body 103 is closed. In such an example, the prosthesis may be attached to the tissue 106 surrounding the trocar tract via at least the proximal end, with the distal end being unattached and sealed. For purposes herein, creating a seal means that solids (e.g., part of an organ) or fluids (e.g., air or other bodily fluids) are prevented from passing into or out of the trocar tract.

Figure 8A:
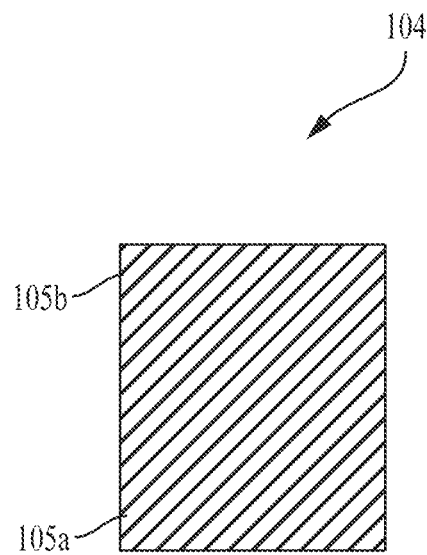
FIG. 8A is a side view of a prosthesis in a delivery configuration.
Figure 8B:
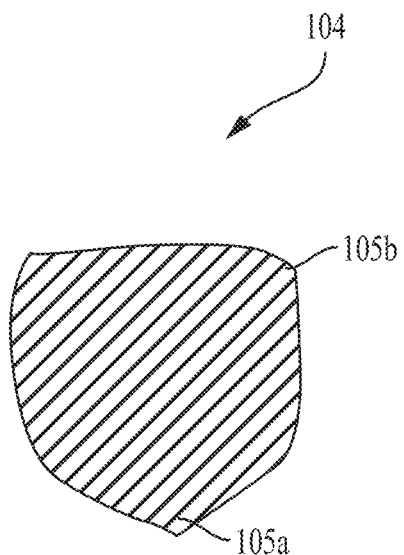
FIG. 8B is a side view of the prosthesis of FIG. 8A in a deployed configuration.

In some embodiments, in the deployed and sealed configuration, as shown in FIGS. 7 and 8B, the outer dimension of the distal end 105a of the body 103 is smaller than the outer dimension of at least the proximal end 105b of the body. In contrast, as shown in FIG. 8A, in the delivery configuration, the prosthesis body may have a constant outer dimension. Turning back to FIG. 8B, in the sealed configuration, the shape of the body may taper to a point at the distal end of the body. In some embodiments, such a tapering may be seen over the last 10% of the length of the prosthesis body. Tapering also may be seen between the last 5% and 40% of the length of the prosthesis body.

Figure 9A:
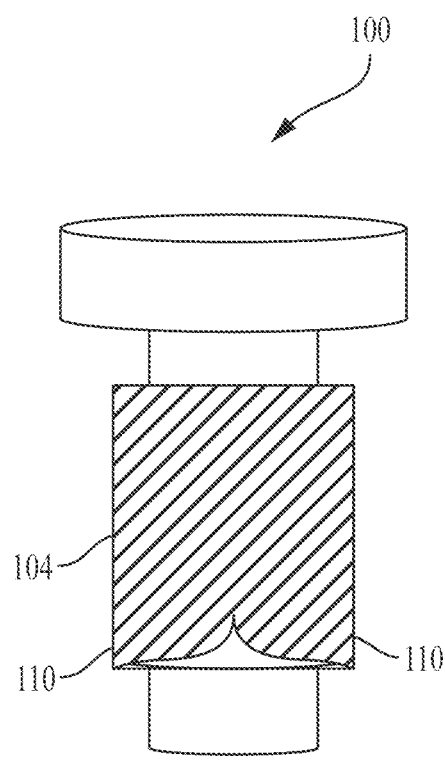
FIG. 9A is a perspective view of a prosthesis removably mounted along a trocar according to one embodiment.
Figure 9B:
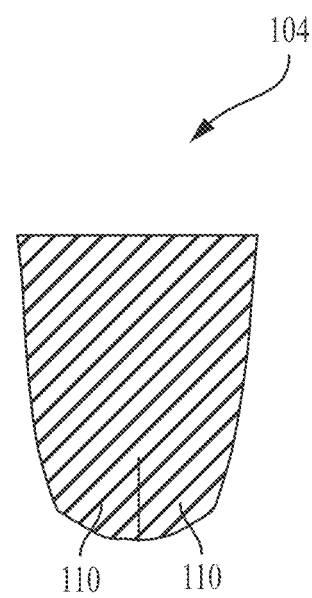
FIG. 9B is a side view of the prosthesis of FIG. 9A in a deployed configuration.

In some embodiments, the distal end may automatically take on the sealed configuration when the prosthesis has been deployed. For example, in some embodiments, the distal end of the prosthesis body 103 may comprise an elastic material that contracts when the trocar is removed from the prosthesis. In other embodiments as shown in FIGS. 9A and 9B, the body 103 may include one or more flaps 110 that are arranged to automatically close when the trocar is removed from the prosthesis. In such embodiments, the flaps may be biased in an outward direction when prosthesis is in the delivery configuration (see FIG. 9A) and move inwardly to close when the prosthesis is in the deployed configuration (see FIG. 9B). The flaps also may overlap one another in the deployed and sealed configuration. In some embodiments, the flaps may overlap one another in the delivery configuration and may assume a greater overlap in the deployed configuration.

In other embodiments, the distal end of the prosthesis may be manually closed to seal the trocar tract. For example, a surgeon may tighten a suture extending along a periphery of the distal end of the prosthesis body to close the distal end. As another example, a surgeon may tighten a suture or wire that extends through the one or more flaps at the distal end of the body.

According to another aspect of the disclosure, the prosthesis includes one or more attachment members or an adhesive to attach the prosthesis to the tissue surrounding the trocar tract when the trocar is inserted and positioned in the trocar tract. As described with respect to FIGS. 6 and 7, such an attachment may hold the prosthesis at the tract when the trocar is removed from the trocar tract.

As will be appreciated, the attachment members and/or adhesive may be positioned on any suitable location of the prosthesis body. For example, the attachment members and/or adhesive may be located on a portion of the body at or near the distal end of the body. The attachment members and/or adhesive also may be located on a portion of the body at or near the proximal end, or a portion of the body between the proximal and distal ends.

As shown in FIGS. 10A and 10B, in some embodiments, the attachment members include one or more flaps 120. As will be appreciated, the flaps 120 may be located at the distal end 105a of the body, although the flaps 120 also may be located at another suitable location, such as between the distal and proximal ends. In some embodiments, the flaps may be the same size, although the size of the flaps may vary from flap to flap. The flaps may have any suitable shape. There may be a uniform distribution of flaps around the body, such that the flaps are spaced evenly around a periphery of the prosthesis body. There also may a non-uniform distribution of flaps around the prosthesis body.

In some embodiments, when the trocar is being inserted into the trocar tract (e.g., the prosthesis is in the delivery configuration), the flaps may be positioned adjacent or against the outer surface of the prosthesis body (see FIG. 10A). In such embodiments, the flaps may be biased in an outward direction such that when the trocar is inserted and positioned in the trocar tract, the flaps may move (e.g., spring) outwardly. For example, in one embodiment, as shown in FIG. 10B, in the outward position, the flaps may extend substantially perpendicular to the longitudinal axis of the prosthesis body, and substantially parallel to an inner surface of the tissue. In such an outward position, the flaps may hold the prosthesis body at the trocar tract when the trocar is removed from the tract. As will be appreciated, the flaps may remain in the outward position when the prosthesis is in the delivery configuration. In some embodiments, the flaps also may be arranged to seal the trocar tract, as described above. For example, the flaps may include a suture that may be manually pulled to form a seal at the trocar tract once the prosthesis has been deployed.

Figure 11:
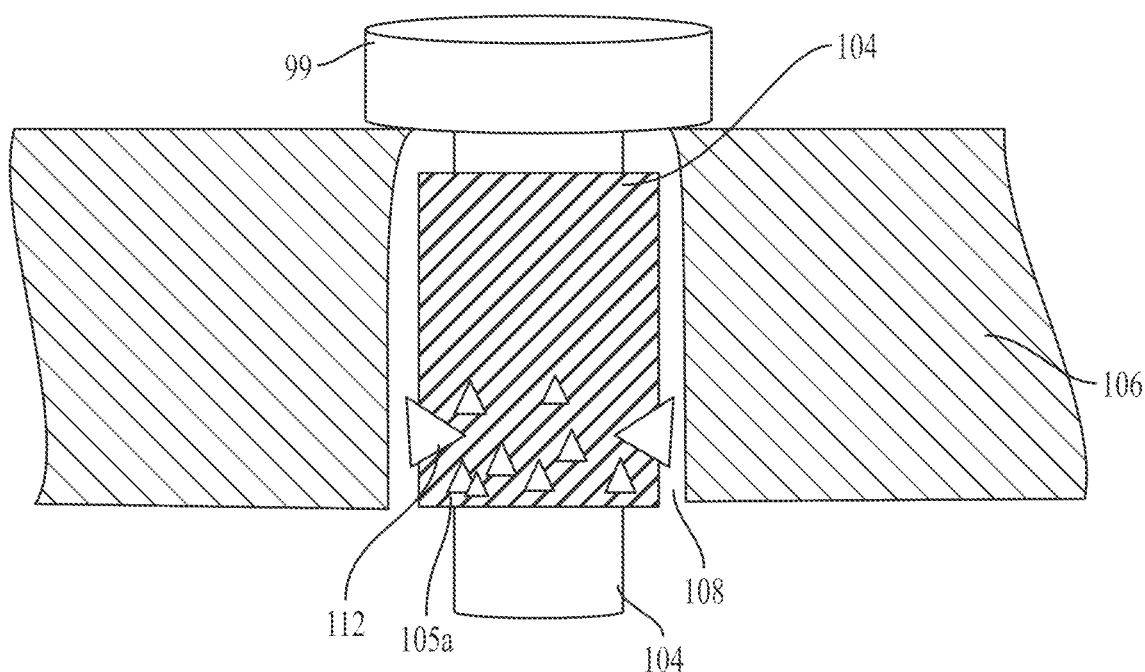
FIG. 11 illustrates a prosthesis removably mounted along a trocar according to another embodiment.

FIG. 11 shows another embodiment, in which the attachment members include a plurality of barbs 112. As shown in this view, in one embodiment, the barbs 112 may be located at the distal end 105a of the prosthesis body 103, although the barbs also may be located at other suitable locations along the body. As will be appreciated, the barbs 112 may be distributed evenly or unevenly along the outer surface of the body 103. In some embodiments, the barbs 112 have a uniform shape and size, although the shape and size of the barbs may vary from barb to bar.

In some embodiments, the barbs 112 may point in an upward direction (e.g., toward the proximal end of the prosthesis body). In such embodiments, the barbs 112 may have a sharp or pointed end. In some embodiments, when the trocar is removed from the trocar tract, the barbs 112 may catch onto or pierce the surrounding tissue, attaching the prosthesis 104 to the tissue and holding the prosthesis at the trocar tract.

Figure 12A:
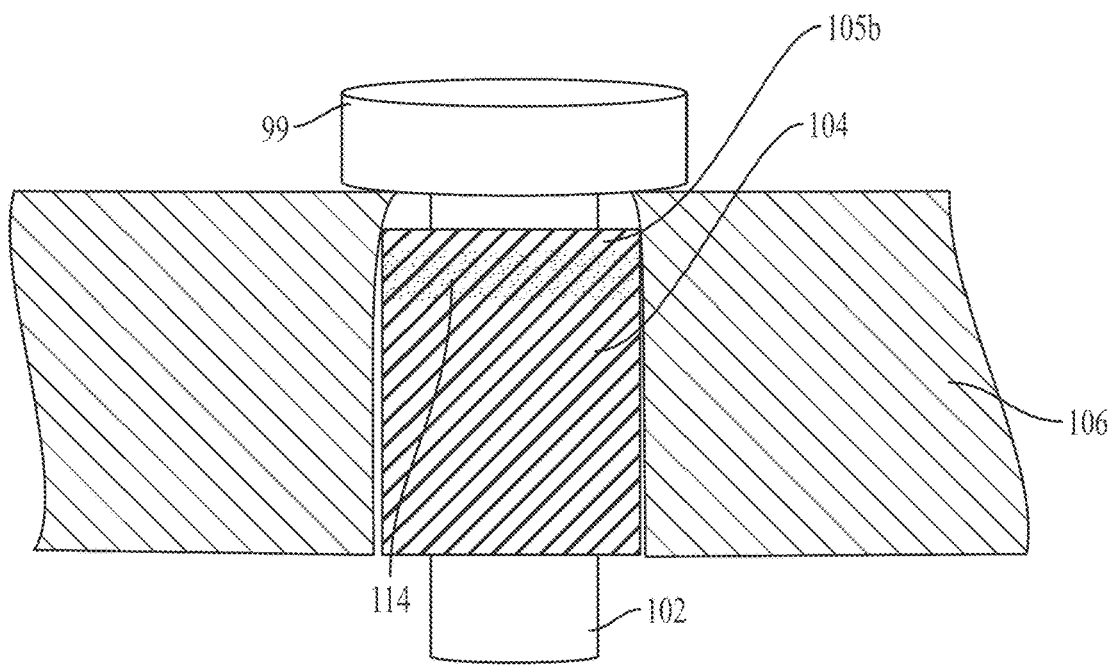
FIGS. 12A and 12B illustrate prostheses removably mounted along trocars according to other embodiments.
Figure 12B:
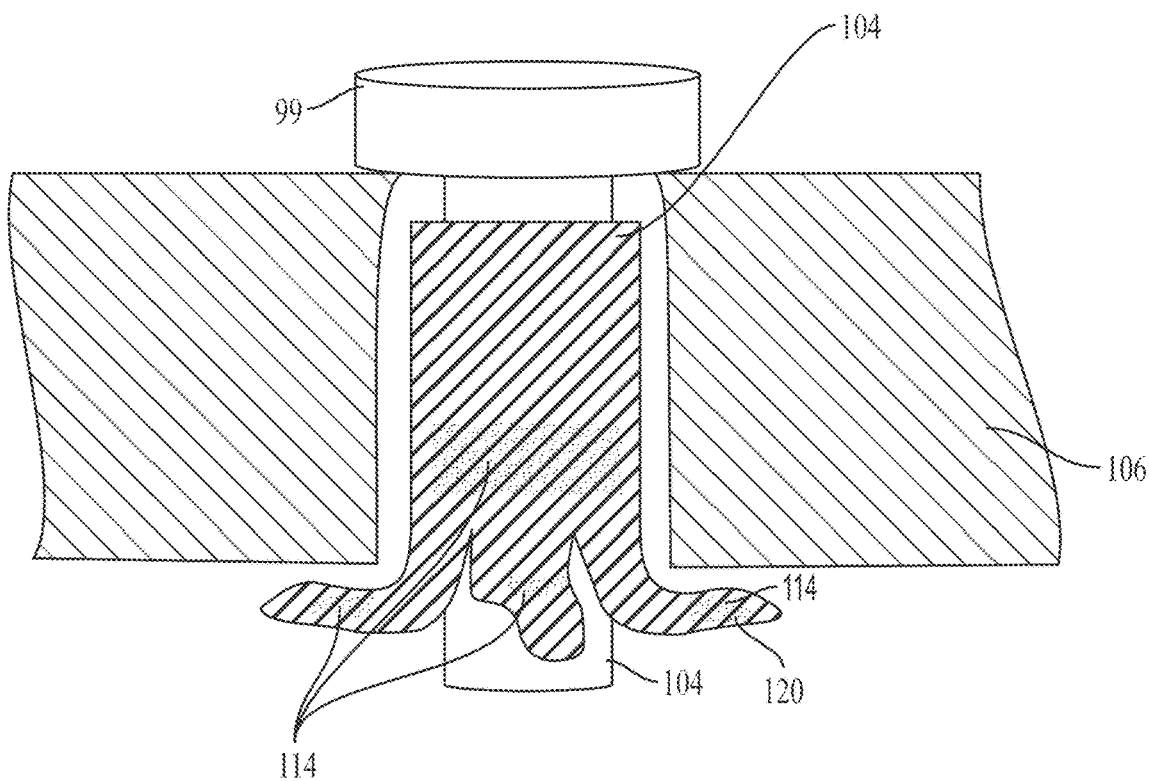

FIGS. 12A and 12B illustrate another embodiment in which an adhesive 114 is used to attach the prosthesis body to the tissue 106 surrounding the trocar tract 108. As shown in these views, the adhesive may be applied to a proximal end 105b of the body, to one or more flaps 120, or to both the body and one or more flaps. As will be appreciated, the adhesive may be applied to the entire outer surface of the prosthesis, or any portion thereof.

In some embodiments, the adhesive includes a tissue activated compound, such as a water-activated compound that adheres to tissue after a period of time. For example after insertion and positioning of the trocar in the trocar tract, the tissue activated compound may be activated to attach the body to the tissue. In some embodiments, the tissue activated compound may require between 2 and 10 minutes for activation and attachment to the tissue, although the compound may be activated in more or less time.

Although the body is shown as having barbs or flaps in FIGS. 9 and 10, it will be appreciated that the body may have both barbs and flaps. In some embodiments, one or more barbs may be positioned on one or more flaps. The body also may have barbs, flaps, an adhesive, or any combination thereof. The adhesive may be applied to both barbs and flaps, although it may be applied to only one or to none.

According to another aspect of the present disclosure, a kit for use in a MIS is provided. In some embodiments, the kit includes a trocar and a prosthesis (or multiple prostheses) that may be mounted along an exterior surface of the trocar. In such embodiments, before or during the MIS, a surgeon may open the kit and may mount a prosthesis along the trocar. In such embodiments, the surgeon may also attach the prosthesis to the trocar (e.g., via one or more fasteners that engage with corresponding fasteners, as described above). The trocar may then be inserted and positioned in the trocar tract.

In some embodiments, at least some or all of the body of the prosthesis may be flexible (e.g., stretchable) such that the body may controllably expand and contract when mounted along the trocar and when plugging or covering the trocar tract, respectively. In some embodiments, some or all of the body may be formed of an elastic material. For example, the prosthesis body may snugly fit the trocar at points of attachment and may be loose elsewhere, although the full length of the prosthesis also may snugly fit the trocar. As will be appreciated, portions of the prosthesis may be formed of different materials and/or have different properties. For example, the body may be formed of a flexible material while the barbs may not be flexible or may be less flexible than the body.

In some embodiments, some or all of the prosthesis body may be formed of a material that is solid or porous. For example, some or all of the body may be a monofilament or multifilament mesh sleeve. As will be appreciated, such a sleeve may have any suitable thicknesses. In some embodiments, the mesh may be tissue infiltratable at one portion or multiple portions to improve tissue growth and recovery. In such an embodiment, the mesh may remain in the tissue indefinitely or may have bioabsorbable properties.

In some embodiments, the entire prosthesis body may be tissue infiltratable and improve tissue growth and recovery. In other embodiments, as will be appreciated, only a portion of the prosthesis body may be tissue infiltratable. For example, only the outer surfaces of the prosthesis body may be tissue infiltratable. In another example, the body but not the attachment members may be tissue infiltratable. In other embodiments, the prosthesis may not be tissue infiltratable. In some embodiments, the prosthesis may dissolve after tissue ingrowth such that only new tissue remains.

In some embodiment, the tissue infiltratable portion has a thickness of between about 0.015 inches and 0.33 inches. For example, in some embodiments, the tissue infiltratable fabric may have a thickness of between about 0.015 inches and 0.1 inches. In such examples, when the repair fabric includes a monofilament or multifilament, the monofilament or multifilament may have a diameter of approximately 0.0043 inches.

In some embodiments, the tissue infiltratable portion may include one or more sheets of a prosthetic repair fabric. Such repair fabric may be formed of a biologically compatible, flexible repair material that includes a plurality of interstices or openings which allow sufficient tissue or muscle ingrowth to integrate the prosthesis with host tissue after implantation. In embodiments having multiple sheets of tissue infiltratable fabric, the multiple sheets may enhance the strength of the prosthesis and/or the amount of tissue ingrowth to the prosthesis. In such embodiments, the one or more sheets of prosthetic repair fabric may be bonded or otherwise joined together to form the tissue infiltratable portion. The one or more sheets may have the same or different thickness and may be made of the same or different materials. As will be appreciated, the prosthesis 104 is not so limited, and one or more sheets may be formed of any biologically compatible material, synthetic or natural, suitable for repairing the trocar tract.

In some embodiments, the body may be loaded with an active pharmaceutical ingredient ("API"). For example, the prosthesis may contain, be coated, or be impregnated with an analgesic or antibiotic. The API may be a powder or liquid that is applied to the prosthesis before the prosthesis 104 is mounted along the cannula.

In some embodiments, the API may be released into the surrounding tissue as soon as the trocar is inserted and positioned in the trocar tract. The API also may be timed for extended release. For example, the API may be releasable into the tissue for between 1 day and three days. In such embodiments, the release of the API may be delayed. For example, the prosthesis 104 may have a biodegradable coating over the API that dissolves with moisture such that the API is not released into the tissue for at least a day. As another example, the removal of the trocar from the trocar tract may activate the release of the API.

In still another embodiment, some or all of the prosthesis may be formed of a knitted fabric. For example, the knit patterns may include a single knit, a double knit, a circular knit, or another suitable knit pattern. In some embodiments, the fabric constructions may include a knitted fabric, a woven fabric, a braided fabric, a non-woven fabric, or another suitable fabric construction.

In some embodiments, the prosthetic repair fabric may include BARD MESH (available from C. R. Bard, Inc.), SOFT TISSUE PATCH, SURGIPRO, TRELEX, PROLENE and MERSILENE, and other mesh materials. Resorbable materials, including polyglactin (VICRYL) and polyglycolic acid (DEXON), may be suitable for applications involving temporary correction of tissue or muscle defects. Collagen materials such as COOK SURGISIS also may be used.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including", "comprising", "having", "containing," or "involving," and variations thereof herein, are meant to encompass the items listed thereafter and equivalents thereof as well as additional item

What is claimed is:

1. An implantable prosthesis in combination with a trocar, the combination comprising: a trocar with a proximal end and a distal end, a respective opening at each end, and a trocar channel extending between the proximal opening and the distal opening for passing one or more surgical instruments through the trocar; and a prosthesis comprising a prosthetic repair fabric, the prosthesis being removably mountable along an outer surface of the trocar, the prosthesis including a tubular body having a proximal end and a distal end, a respective opening at each of the proximal end and the distal end of the tubular body, and a prosthesis channel extending between the proximal end and the distal end of the tubular body, wherein the prosthesis includes a delivery configuration where the prosthesis is removably mounted along the outer surface of the trocar and a deployed configuration where the prosthesis is completely removed from the trocar, wherein, in the deployed configuration, the opening at the distal end of the tubular body is configured to close to form a fluid-tight seal at the distal end of the tubular body, the proximal end of the tubular body remaining open in the deployed configuration, and wherein the opening at the distal end of the tubular body is smaller in the deployed configuration than in the delivery configuration, wherein the prosthesis repair fabric is resorbable.

2. The combination of claim 1, wherein, in the delivery configuration, the opening at the distal end of the tubular body is the same size as the opening at the proximal end of the tubular body.

3. The combination of claim 1, wherein the distal end of the tubular body includes one or more flaps.

4. The combination of claim 3, wherein, in the deployed configuration, the one or more flaps are arranged to overlap one another.

5. The combination of claim 4, wherein, in the deployed configuration, the one or more flaps overlap one another to form the fluid-tight seal.

6. The combination of claim 3, wherein the one or more flaps bias in a closed position.

7. The combination of claim 6, wherein, in the delivery configuration, the one or more flaps are movable in an outward direction when a surgical instrument is inserted through the trocar.

8. The combination of claim 1, wherein the tubular body includes one or more attachment members arranged to attach the prosthesis to a tissue surrounding a trocar tract.

9. The combination of claim 8, wherein the one or more attachment members are located at a portion at or near the distal end of the tubular body.

10. The combination of claim 9, wherein the one or more attachment members are located around at least a portion of a perimeter of the portion at or near the distal end of the tubular body.

11. The combination of claim 8, wherein the one or more attachment members include one or more flaps and/or one or more barbs.

12. The combination of claim 11, wherein, in the delivery configuration, the one or more flaps are positioned against an outer surface of the tubular body.

13. The combination of claim 12, wherein, in the deployed configuration, the one or more flaps extend outwardly from a portion at or near the distal end of the tubular body.

14. The combination of claim 13, wherein, in the deployed configuration, the one or more flaps extend substantially perpendicular to a longitudinal axis of the tubular body.

15. The combination of claim 11, wherein the one or more barbs point in a direction towards the proximal end of the tubular body.

16. The combination of claim 11, wherein the one or more barbs are located on one or more flaps at a portion at or near the distal end of the tubular body.

17. The combination of claim 12, wherein the one or more flaps bias in an outward direction, wherein, in the delivery configuration, when the trocar is inserted and positioned in the trocar tract, the one or more flaps are moveable outwardly from a portion at or near the distal end of the tubular body.

18. The combination of claim 1, wherein the tubular body includes an adhesive arranged to attach the tubular body to a tissue surrounding a trocar tract.

19. The combination of claim 18, wherein the adhesive is moisture activated.

20. The combination of claim 18, wherein the adhesive is applied to one or more flaps at a portion at or near the distal end of the tubular body.

21. The combination of claim 18, wherein the adhesive is applied to a portion of an exterior surface of the tubular body.

22. The combination of claim 1, wherein the tubular body is stretchable.

23. The combination of claim 1, wherein the tubular body is coated or impregnated with an active pharmaceutical ingredient.

24. The combination of claim 1, wherein, in the delivery configuration, the distal end of the tubular body covers the distal end of the trocar.

25. The combination of claim 1, wherein the prosthesis channel extends between the opening at the proximal end of the tubular body and the opening at the distal end of the tubular body.

26. The combination of claim 1, wherein the trocar includes an integrally formed trocar.

27. The combination of claim 1, wherein the trocar includes a trocar and cannula assembly.

28. The combination of claim 1, wherein the trocar includes a cannula.

29. A method comprising: providing a trocar with a proximal end and a distal end, a respective opening at each end, and a trocar channel extending between the proximal opening and the distal opening for passing one or more surgical instruments through the trocar; removably mounting a prosthesis comprising a prosthetic repair fabric along an outer surface of the trocar, the prosthesis having a tubular body with a distal end and a proximal end, a respective opening at each of the proximal end and the distal end of the tubular body, and a prosthesis channel extending between the proximal end and the distal end of the tubular body, wherein the prosthesis includes a delivery configuration where the prosthesis is removably mounted along the outer surface of the trocar and a deployed configuration where the prosthesis is completely removed from the trocar; and closing the opening at the distal end of the tubular body to form a fluid-tight seal when the tubular body is in the deployed configuration, the proximal end of the tubular body remaining open in the deployed configuration, wherein the prosthetic repair fabric is resorbable.

30. The method of claim 29, further comprising inserting the trocar along a tract through tissue, wherein the prosthesis is in the delivery configuration.

31. The method of claim 30, further comprising removing the trocar from the tract.

32. The method of claim 31, further comprising removing the trocar from the prosthesis, wherein the prosthesis is in the deployed configuration.

33. The method of claim 30, further comprising attaching the tubular body to tissue surrounding the tract via one or more flaps and/or one or more barbs located on the tubular body.

34. The method of claim 30, further comprising attaching the tubular body to tissue surrounding the tract via an adhesive.

35. The method of claim 34, wherein the adhesive includes a tissue reactive component.

36. The method of claim 33, wherein the one or more flaps and/or one or more barbs are located at a portion at or near the distal end of the tubular body.

37. The method of claim 33, wherein the one or more barbs point in a direction towards the proximal end of the tubular body.

38. The method of claim 33, wherein, in the delivery configuration, the one or more flaps are positioned against an outer surface of the tubular body.

39. The method of claim 33, where, in the deployed configuration, the one or more flaps extend outwardly from a portion at or near the distal end of the tubular body.

40. The method of claim 29, wherein closing the opening includes overlapping one or more flaps located at a portion at or near the distal end of the tubular body.

* * * * *